US009387028B2

(12) United States Patent
Olson et al.

(10) Patent No.: US 9,387,028 B2
(45) Date of Patent: Jul. 12, 2016

(54) BONE SCREW WITH CHANNELS

(71) Applicants: Jon Olson, Houston, TX (US); Chad Steitle, Houston, TX (US)

(72) Inventors: Jon Olson, Houston, TX (US); Chad Steitle, Houston, TX (US)

(73) Assignee: Trilliant Surgical, Ltd., Houston, TX (US)

( * ) Notice: Subject to any disclaimer, the term of this patent is extended or adjusted under 35 U.S.C. 154(b) by 67 days.

(21) Appl. No.: 14/308,290

(22) Filed: Jun. 18, 2014

(65) Prior Publication Data

US 2014/0303677 A1    Oct. 9, 2014

Related U.S. Application Data

(62) Division of application No. 12/372,042, filed on Feb. 17, 2009, now abandoned.

(51) Int. Cl.
*A61B 17/86* (2006.01)
*A61B 17/56* (2006.01)

(52) U.S. Cl.
CPC ........... *A61B 17/864* (2013.01); *A61B 17/8625* (2013.01); *A61B 17/8645* (2013.01); *A61B 2017/564* (2013.01); *A61B 2017/8655* (2013.01)

(58) Field of Classification Search
CPC ............. A61B 17/864; A61B 17/8645; A61B 17/8625; A61B 2017/8655; A61B 2017/564
USPC ........ 606/301, 304, 309, 316; 411/387.7, 424
See application file for complete search history.

(56) References Cited

U.S. PATENT DOCUMENTS

| | | | | |
|---|---|---|---|---|
| 45,133 A * | 11/1864 | Bonwill | ............... | F16B 25/0015 411/421 |
| 877,131 A * | 1/1908 | Searelle | ................... | F16B 35/06 411/399 |
| 1,235,626 A * | 8/1917 | Woodward | .......... | F16B 25/0078 411/421 |
| 4,463,753 A * | 8/1984 | Gustilo | ................ | A61B 17/863 411/386 |
| 4,687,443 A * | 8/1987 | Driskell | ............... | A61C 8/0018 433/173 |
| 4,697,969 A * | 10/1987 | Sparkes | ............. | F16B 25/0015 411/387.7 |
| 5,129,901 A | 7/1992 | Decoste | | |
| 5,169,400 A | 12/1992 | Muhling | | |

(Continued)

FOREIGN PATENT DOCUMENTS

| | | |
|---|---|---|
| EP | 0788781 | 8/1997 |
| EP | 0988833 | 3/2000 |

(Continued)

OTHER PUBLICATIONS

International Searching Authority, Notification of Transmittal of the International Search Report, mailed Sep. 27, 2010, in International Application No. PCT/US2010/023715.

(Continued)

*Primary Examiner* — Zade Coley
(74) *Attorney, Agent, or Firm* — Trop, Pruner & Hu, P.C.

(57) ABSTRACT

Embodiments of the invention may prevent or diminish a bone screw from "backing out" from bone. Bone particulate residing in channels of the bone screw may promote bone growth that would reduce the potential of backing out. Furthermore, bone particulate from drilling and tapping functions can cause increased friction. However, by placing bone particulate in channels of the bone screw, potential binding may be reduced resulting in less stress on the screw shaft. Also, breaking of screws during screw insertion may be reduced due to tapering of the screw.

20 Claims, 3 Drawing Sheets

(56) References Cited

U.S. PATENT DOCUMENTS

| | | | |
|---|---|---|---|
| 5,300,076 A | | 4/1994 | Leriche |
| 5,334,204 A | * | 8/1994 | Clewett .............. A61B 17/8625 606/312 |
| 5,425,407 A | * | 6/1995 | Archuleta ............... B29C 73/06 152/370 |
| 5,562,672 A | | 10/1996 | Huebner |
| 5,797,914 A | | 8/1998 | Leibinger |
| 5,800,101 A | * | 9/1998 | Jindai .................... B23B 51/02 408/227 |
| 5,868,749 A | * | 2/1999 | Reed ...................... A61B 17/80 606/104 |
| 5,964,768 A | | 10/1999 | Huebner |
| 6,048,343 A | | 4/2000 | Mathis |
| 6,129,730 A | | 10/2000 | Bono |
| 6,187,008 B1 | | 2/2001 | Hamman |
| 6,375,657 B1 | | 4/2002 | Doubler |
| 6,540,752 B1 | * | 4/2003 | Hicken ................ A61B 17/885 606/90 |
| 6,551,323 B2 | | 4/2003 | Doubler |
| 7,207,994 B2 | | 4/2007 | Vlahos |
| 7,293,947 B2 | * | 11/2007 | Craven ................ F16B 35/065 411/387.2 |
| 7,338,493 B1 | | 3/2008 | Vandewalle |
| 2004/0044345 A1 | | 3/2004 | DeMoss |
| 2006/0009770 A1 | | 1/2006 | Speirs |
| 2006/0129147 A1 | * | 6/2006 | Biedermann ...... A61B 17/7004 128/897 |
| 2006/0149263 A1 | | 7/2006 | Newcomb |
| 2006/0241623 A1 | * | 10/2006 | Lim .................... A61B 17/8625 606/265 |
| 2007/0055257 A1 | | 3/2007 | Vaccaro |
| 2007/0162028 A1 | | 7/2007 | Jackson |
| 2008/0051793 A1 | | 2/2008 | Erickson |
| 2008/0177331 A1 | | 7/2008 | Perez-Cruet |

FOREIGN PATENT DOCUMENTS

| | | |
|---|---|---|
| WO | WO0028907 | 5/2000 |
| WO | WO0117447 | 3/2001 |
| WO | WO02065925 | 8/2002 |
| WO | WO2008085985 | 7/2008 |
| WO | WO2008097403 | 8/2008 |
| WO | WO2008100239 | 8/2008 |
| WO | WO2010096308 | 8/2010 |

OTHER PUBLICATIONS

Canadian Intellectual Property Office, Office Action mailed Dec. 17, 2012 in Canadian Application No. 2,752,685.

United States Patent and Tredemark Office "File History" excerpts from U.S. Appl. No. 10/712,202, filed Nov. 12, 2013 by Randall J. Huebner, 55 pages.

* cited by examiner

BONE SCREW WITH CHANNELS

This application is a divisional of U.S. patent application Ser. No. 12/372,042, filed Feb. 17, 2009, the content of which is hereby incorporated by reference.

BACKGROUND

Cannulated bone screws are available in self-drilling and self-tapping screw versions. Such screws may vary in wall thickness, diameter and length, may be fully or partially threaded, and may utilize various head and thread designs as well as any number of materials. However, such screws are less than ideal because, for example, they are prone to fracture and "backing out" of the bone in which they are implanted.

BRIEF DESCRIPTION OF THE DRAWINGS

The accompanying drawings, incorporated in and constituting a part of this specification, illustrate one or more implementations consistent with the principles of the invention and, together with the description of the invention, explain such implementations. The drawings are not necessarily to scale, the emphasis instead being placed upon illustrating the principles of the invention. In the drawings.

DETAILED DESCRIPTION

The following description refers to the accompanying drawings. Among the various drawings the same reference numbers may be used to identify the same or similar elements. While the following description provides a thorough understanding of the various aspects of the claimed invention by setting forth specific details such as particular structures, architectures, interfaces, and techniques, such details are provided for purposes of explanation and should not be viewed as limiting. Moreover, those of skill in the art will, in light of the present disclosure, appreciate that various aspects of the invention claimed may be practiced in other examples or implementations that depart from these specific details. At certain junctures in the following disclosure, descriptions of known devices and methods have been omitted to avoid clouding the description of the present invention with unnecessary detail.

Figure 1:
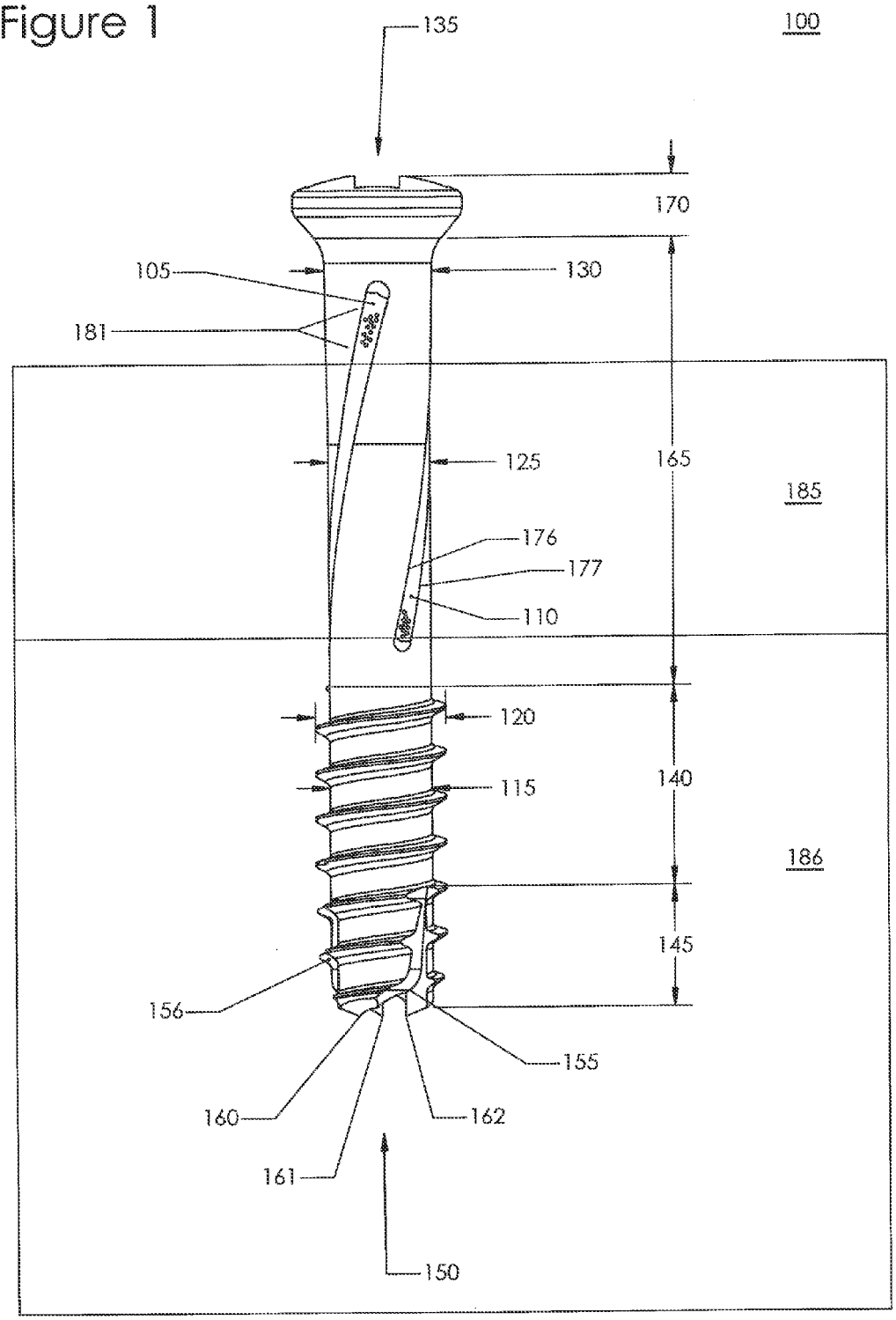
FIG. 1 includes a side view of a device in one embodiment of the invention.

FIG. 1 includes a side view of a bone screw 100 in one embodiment of the invention which may help reduce any counter rotation that may lead to the screw backing out. Furthermore, screw 100 may be more robust and prevent screw failure (e.g., shearing, torsion) during, for example, screw insertion.

Bone screw 100 may comprise a proximal head portion 170 and a distal tip portion 150. A threaded portion, included between the head 170 and tip 150 portions, includes a first segment 140 comprising contiguous threads. For example, such contiguous threads are not interrupted by a channel present on or in the exterior of the screw. Contiguous threading may increase bone purchase and screw integrity in some instances. A non-threaded portion 165, which may be included between the head 170 and threaded 140, 145 portions, may include one or more channels, such as first and second channels 105, 110. A cannula 175 (e.g., a central bore, FIG. 2) may be coterminous with the screw head 135 and distal screw tip 150 portion and may be non-coterminous with the non-threaded 165 and threaded portion(s) (e.g., 140) and the first and/or second channels 105, 110. The head portion 170 and threaded portions 140, 145 may not, in some embodiments of the invention, include first and/or second channels 105, 110. Channel location may increase screw integrity and bone purchase in some instances.

In one embodiment of the invention, bone screw 100 may taper outwardly at or near, for example, head portion 170. For example, threaded portions 140, 145 may include an outer thread diameter 120, which extends to the outermost part or crest of respective threads. Threaded portions 140, 145 may also include an inner thread diameter 115, which may extend to the innermost part or trough of respective threads. Also, non-threaded portion 165 may include diameter 125 that is greater than inner thread diameter 115. In some embodiments, diameter 125 may be greater than outer diameter 120. In an embodiment of the invention, non-threaded portion 165 is tapered to include a gradual increasing of diameters. However, the transition between different diameters need not necessarily be graduated and may be, for example, abrupt. In an embodiment of the invention, diameter 130 may be greater than diameter 125. Tapering may take place across any or all of regions 145, 140, 165, 170. Again, in some embodiments there may be no tapering but varying diameters nonetheless. For example, a diameter for a non-threaded portion may be larger than an inner thread diameter, despite a lack of tapering. In various embodiments, channels 105, 110 may be tapered. For example, channel 105 may include a distal region with a diameter that is smaller than the diameter at a proximal region of channel 105.

Channels 105, 110 may include sharp edges that may, for example, cut bone. For example, channel 110 may include a sharp edge or portion 177 to cut bone during clockwise screw insertion. Channel 110 may also include a sharp edge or portion 176 to cut bone during counter-clockwise screw withdrawal. Channel 110 may include multiple sharp edges 176, 177. Some or all channels in a screw may include one or more such sharp edges or portions.

Again, bone screw 100 may include a threaded portion with threaded segment 145 distal to threaded segment 140. Distal segment 145 may include non-contiguous threads due to the presence of, for example, cutting flutes 155, 156. Flutes 155, 156 (and others not visible in FIG. 1) may terminate in points 160, 161, 162. Furthermore, channels 105, 110 may be helical and wrap or revolve partially or fully around screw 100. Various embodiments may include one channel or numerous other channels (e.g., 3, 4 or more channels). Such channels may be placed horizontally, vertically, or in various other orientations in addition to helical orientations. As described further below, screw 100 may be a lag screw. In addition, bone screw may be headless. If a head is included, such head may be low profile and/or slightly chamfered beneath the screw head to add torsional strength. In various embodiments, threaded portions 140, 145 may include threads that are cut with a trailing edge on the threads to reduce any counter rotation that may lead to the screw backing out.

Figure 2:
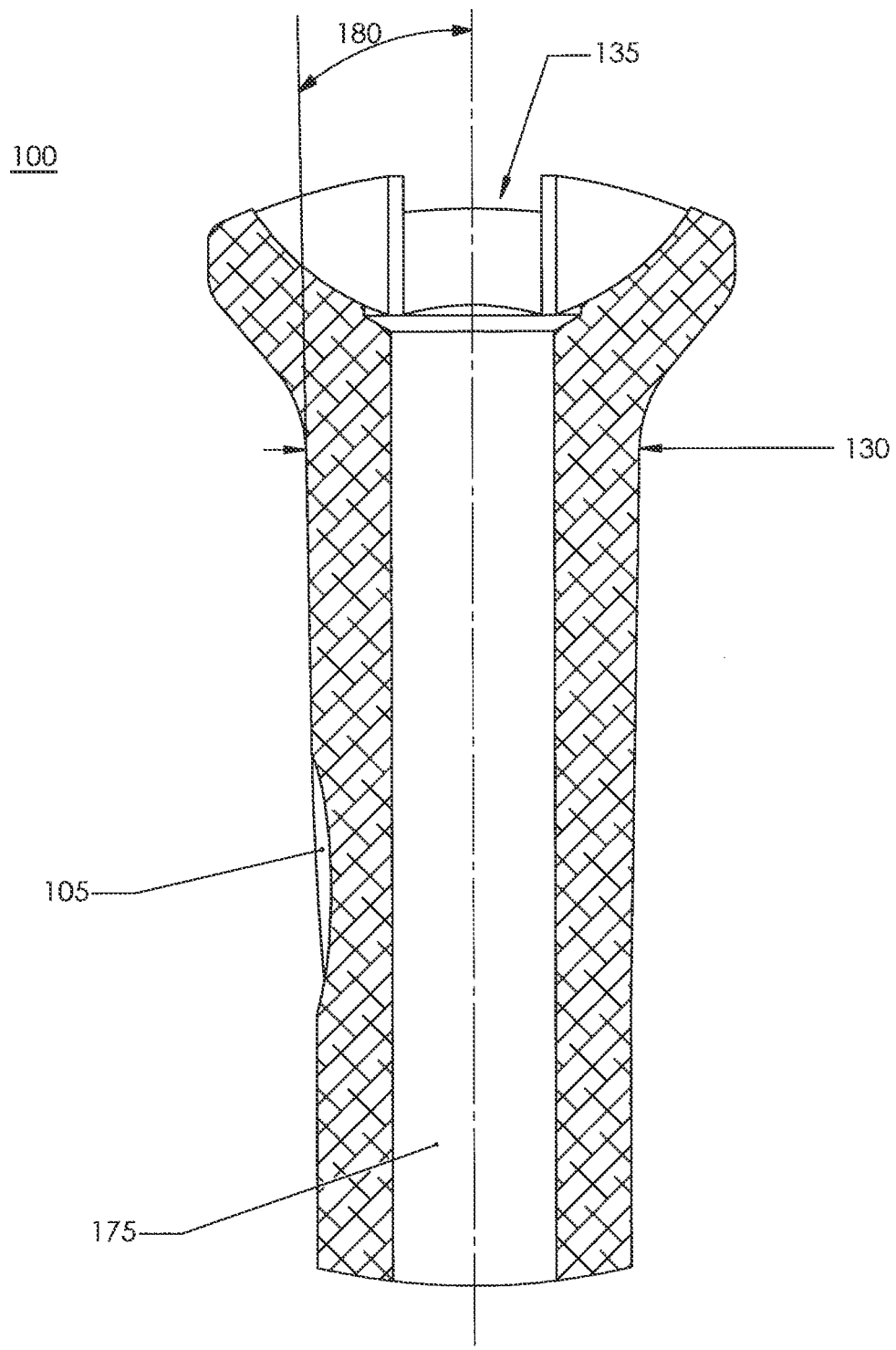
FIG. 2 includes a side view of a device in one embodiment of the invention.

FIG. 2 includes a side view of a device in one embodiment of the invention. Screw 100 may be tapered as indicated by angle 180. Angle 180 may be, for example, one degree rotated away from a central longitudinal axis. A tapered shaft may result, for example, in a 10% greater wall thickness for small diameter screws (e.g., 2.0 mm).

Figure 3:
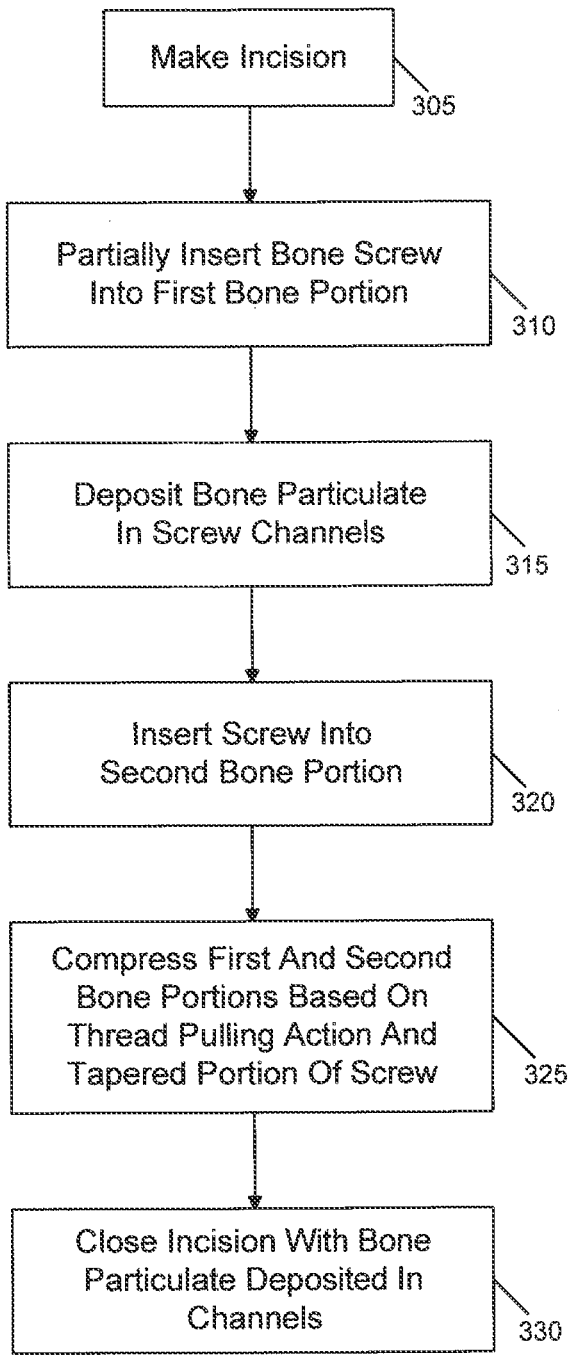
FIG. 3 includes a method in one embodiment of the invention.

FIG. 3 includes a method 300 in one embodiment of the invention. In block 305, an incision may be made by a physician. In block 310, the physician may partially insert a cannulated bone screw (e.g., bone screw 100) into first bone portion 185 (FIG. 1). In block 315, bone particulate 181 may be generated as a result of screw insertion. Such insertion may be eased by sharp edge 177. Such bone particulate may be deposited in first and second channels 105, 110. In block 320, screw 100 may be inserted into second bone portion 186. In block 325, first bone portion 185 may be compressed against second bone portion 186 based on inserting outwardly tapered portions (see, e.g., diameters 125, 130) of non-threaded portion 165 of screw 100 into first bone portion 185. In other words, due to pulling action of threaded portions 140, 145, and the resistance provided by tapered diameters 125, 130, bone segments 185, 186 may be compressed by lag screw 100. In block 330, the incision may be closed while bone particulate 181 is left deposited in first and second channels 105, 110. Accordingly, in one embodiment of the invention, a partially threaded bone screw 100 (FIG. 1) may be used with a lag technique such that non-threaded portion 165 is allowed to turn without binding, or reduced binding, while threaded portion(s) 140, 145 continue to approximate distal bone section 186 until tight against proximal bone section 185. This may be done while using a bone clamp to compress relevant bone sections 185, 186 so as to not distract distal segment 186 as the lag effect may not be seen (or seen to a relevant extent) until tapered non-threaded portion 165 of screw 100, or even head portion 170, is seated against proximal bone segment 185 or ancillary hardware such as a plate, which may be countersunk in some embodiments. With a tapered shaft existing through any or all portions of screw 100 (e.g., portions 165 and 170), the interference due to the tapered diameters may begin a lag effect before head portion 170 of the screw is fully seated. Also, the interference fit may help distribute the stress and load of the lag stress and alleviate some tendency for fracture of the bone at, for example, the bone/screw head interface.

Various methods may be practiced with various embodiments of the invention. The surgeon may use a bone clamp to create the necessary compression across, for example, an osteotomy or fusion site. The surgeon may insert an appropriately sized guide wire to the correct length under image intensification. The wire may be inserted in 15 mm-20 mm increments. The surgeon may slide the appropriately sized depth gauge/countersink over the guide wire until the countersink tip contacts bone. The surgeon may rotate the countersink back and forth to create the necessary recess in the bone. The surgeon may measure for the desired screw length by examining the end of the guide wire in relation to the marks on the depth gauge. For 3.0 mm & 4.0 mm screws in dense cortical bone, pre-drilling the near cortex using the cannulated drill may help reduce the axial force necessary for inserting the screw. The surgeon may select the desired cannulated screw and slide the same over the guide wire. Then, using a screw driver and appropriate driver shaft, he or she may drive the screw into bone until the desired compression is achieved. The surgeon may then remove and discard the guide wire.

Another method may include use of, for example, screws for arthrodesis of the 2nd through 5th digits. The surgeon may expose the joint space dorsal of the proximal interphalangeal joint and resect the articular surfaces of the proximal interphalangeal joint. He or she may use a wire pin driver and a 0.035" double trocar K-wire, insert the K-wire centrally into the middle phalanx, and drill towards the distal phalanx. The surgeon may position the distal phalanx in the desired position and continue inserting the K-wire, maintaining a central position. He or she may continue driving proximal to distal until the K-wire is protruding through the distal phalanx. After assurance that the K-wire is sufficiently exposed to allow for capture with the wire pin driver, the surgeon may, with the wire pin driver, retract the K-wire until the proximal end is only exposed 1 to 2 mm. He or she may then extend the digit to obtain proper alignment between the K-wire and the proximal phalanx. The surgeon may then drive the K-wire to engage the proximal phalanx, assuring that the K-wire does not pass into the metatarsophalangeal joint. The surgeon may countersink if desired and bone surface is adequate. He or she may use the appropriate depth gauge to determine screw length and, if necessary in dense bone, drill using the appropriate cannulated drill. He or she may then place the screw on the K-wire and drive the screw until fully seated and then remove the K-wire and discard the same.

Another method may be used for Arthrodesis of the 2nd through 5th digits. For example, a 0.062" K-wire may be used in place of a 0.035" K-wire. The surgeon may replace the 0.062" K-wire with the 0.035" K-wire and ensure that 0.035" K-wire follows pilot hole created by 0.062" K-wire. This may alleviate a need to drill in dense bone using the appropriate cannulated drill as described immediately above.

In one method of use for screw removal, the surgeon may locate the implant with intra-operative imaging and palpate the head portion of the screw and remove surrounding soft tissue to gain maximum exposure to the screw. He or she may then engage the screw head portion with an appropriate driver and rotate counterclockwise until the screw is removed. If the screw is integrated into bone, he or she may need to core out the screw with a trephine drill, although embodiments described above may alleviate the need for such coring.

Various embodiments of the invention may include a system of screws used for bone fixation of the hand and foot following trauma or osteotomy. Cannulated, threaded bone screws may include, for example, 2.0, 2.4, 3.0 & 4.0 mm diameters with lengths of 8-56 mm. Available screws and instrumentation may be packaged as a single system or the screws may be offered in a single sterile packaged offering. The system instruments may include drill bits, drill guides, guide wires, depth gauges, countersinks, bone clamps, forceps, screw removal tools, and screwdrivers to facilitate the placement of the screws. Screws may be made from, for example, Titanium Alloy (ASTM F-136). Instrumentation may be made from, for example, medical grades of titanium, stainless steel, anodized aluminum, and plastic.

Thus, as indicated above, various embodiments of the invention may prevent or diminish a bone screw from "backing out" from the bone. Bone particulate residing in channels 105, 110 may promote bone growth that would reduce the potential of backing out. For bone tissue remodeling, bone particulate 181 may incorporate into new growth providing ingrowth of the bone (e.g., cortical bone under the head of the screw). Channels 105, 110 may add additional surface area for bone integration as compared to previously known technologies. This ingrowth may provide some level of resistance to revolution or axial movement to alleviate tendencies of backing out.

Furthermore, bone particulate from drilling and tapping functions can cause increased friction. This friction can necessitate greater driving torque on the screw shaft for screw insertion, which may lead to screw fractures and failures. By placing or clearing bone particulate in or to channels 105, 110, potential binding may be reduced resulting in less stress on the screw shaft.

Also, with cannulated screws there may be a tradeoff between cannulated wall thickness and available thread height. The balancing of wall thickness and thread height may lead to a design where the head of the screw is prone to breaking or twisting. Such breaking or twisting may be reduced due to the tapering and/or increased proximal diameters described above. For example, tapering may allow for maximum thread height (thinnest wall) in the thread area while reinforcing the portion below or near the head for greater strength. Furthermore, channels may increase flexural strength of screw 100 as compared to previously known technologies.

The above advantages may be particularly relevant for small bone surgery (e.g., ankle, foot). For example, such screws and related instrumentation may be used, for example, for fixation of fractures, non-unions, arthrodeses and osteotomies of the small bones in the hand and foot. However, the various embodiments of the invention are not limited to use in small bone surgery.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
    creating an incision and producing bone particulate based on partially inserting a cannulated bone screw into a first bone portion;
    depositing the bone particulate in first and second channels included entirely in a non-threaded portion of the screw that is proximal to a contiguously threaded portion of the screw;
    inserting the screw into a second bone portion;
    compressing the first bone portion against the second bone portion based on inserting an outwardly tapered portion of the non-threaded portion of the screw into the first bone portion; and
    closing the incision while the bone particulate is deposited in the first and second channels;
    wherein the screw comprises:
        a proximal bone screw head portion and a distal tip portion;
        a threaded portion, included between the head and tip portions, including a first segment comprising the contiguously threaded portion; and
        a cannula that (a) is coterminous with the head and tip portions; (b) is non-coterminous with the threaded and non-threaded portions; (c) does not directly connect with the first and second channels, (d) includes a long axis extending from the head portion to the tip portion, and (e) forms a sidewall between the cannula and an outer edge of the screw, the sidewall including a first sidewall thickness, measured orthogonally to the long axis, for the threaded portion that is thinner than a second sidewall thickness for the non-threaded portion;
    wherein the head and threaded portions do not include the first and second channels;
    wherein the threaded portion includes an outer thread diameter and an inner thread diameter and the non-threaded portion, which includes at least one of the first and second channels, includes a diameter that is greater than the inner thread diameter;
    wherein the non-threaded portion is tapered along the first and second channels, the first and second channels each having constant widths.

2. The method of claim 1, further comprising cutting the first bone portion with a sharp edge included in the first channel during insertion of the screw into the first bone portion.

3. The method of claim 1, further comprising closing the incision while the first channel is adjacent cortical bone to promote integration between cortical bone and the bone particulate included in the first channel.

4. The method of claim 1, wherein the diameter is measured along a horizontal axis that intersects the first channel.

5. The method of claim 4, wherein the screw tapers outwardly near the head portion, the first bone portion includes one of a distal and a proximal phalanx and the second bone portion includes another of the distal and proximal phalanx.

6. The method of claim 5, wherein the threaded portion includes a second segment distal to the first segment, the second segment comprising non-contiguous threads and a plurality of cutting flutes.

7. The method of claim 1, wherein the first sidewall thickness is the thinnest sidewall thickness for the screw.

8. The method of claim 1, wherein the first sidewall thickness extends outwardly up to, but not beyond, the inner thread diameter.

9. The method of claim 1, wherein the diameter is measured along a horizontal axis that intersects the first channel.

10. A method comprising:
    creating an incision and producing bone particulate based on partially inserting a cannulated bone screw into a first bone portion;
    depositing the bone particulate in first and second channels included entirely in a non-threaded portion of the screw that is proximal to a contiguously threaded portion of the screw;
    inserting the screw into a second bone portion;
    compressing the first bone portion against the second bone portion based on inserting an outwardly tapered portion of the non-threaded portion of the screw into the first bone portion; and
    closing the incision while the bone particulate is deposited in the first and second channels
    wherein the screw includes:
    a cannula that is (a) coterminous with proximal and distal ends of the screw and (b) not directly connected to the first and second channels;
    wherein the first and second channels taper away from the cannula along the majority of their entire lengths and sidewalls of the first channel are consistently spaced from one another along the majority of the entire length of the first channel;
    wherein the threaded portion includes an outer thread diameter and the non-threaded portion has a diameter, measured along a horizontal axis that intersects the first channel, which is greater than the outer thread diameter.

11. The method of claim 10 comprising countersinking the screw, wherein the first and second channels are excluded entirely from the threaded portion.

12. The method of claim 10, wherein the non-threaded portion tapers outwardly.

13. The method of claim 10, wherein sidewall thickness for the screw is thinnest in the threaded portion where maximum thread height for the screw is located.

14. The method of claim 10, wherein the diameter is measured approximately half way along the length of the first channel.

15. The method of claim 10, wherein the diameter is measured at a point located between approximately a third from a bottom of the first channel and a third from a top of the first channel.

16. A method comprising:
creating an incision and producing bone particulate based on partially inserting a cannulated bone screw into a first bone portion;
depositing the bone particulate in first and second channels included in a non-threaded portion of the screw that is proximal to a contiguously threaded portion of the screw;
inserting the screw into a second bone portion;
compressing the first bone portion against the second bone portion based on inserting an outwardly tapered portion of the non-threaded portion of the screw into the first bone portion; and
closing the incision while the bone particulate is deposited in the first and second channels;
wherein the screw includes:
a cannula that is (a) coterminous with proximal and distal ends of the screw and (b) not directly connected to the first and second channels;
wherein the first and second channels taper away from the cannula along their entire lengths and sidewalls of the first channel are consistently spaced from one another along the majority of the entire length of the first channel;
wherein the threaded portion includes an inner thread diameter and the non-threaded portion has a diameter, measured along a horizontal axis that intersects the first channel, which is greater than the inner thread diameter.

17. The method of claim 16, wherein the threaded portion is not tapered.

18. The method of claim 16, wherein the screw is headless.

19. The method of claim 16, wherein sidewall thickness for the screw is thinnest in the threaded portion where maximum thread height for the screw is located.

20. The method of claim 16, wherein the diameter is measured at a point located between approximately a third from a bottom of the first channel and a third from a top of the first channel.

* * * * *